US009180230B2

(12) United States Patent
Wilkes

(10) Patent No.: US 9,180,230 B2
(45) Date of Patent: Nov. 10, 2015

(54) SYSTEM AND METHOD FOR DELIVERING REDUCED PRESSURE TO SUBCUTANEOUS TISSUE

(71) Applicant: KCI Licensing, Inc., San Antonio, TX (US)

(72) Inventor: Robert Peyton Wilkes, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 189 days.

(21) Appl. No.: 13/853,820

(22) Filed: Mar. 29, 2013

(65) Prior Publication Data
US 2013/0289502 A1 Oct. 31, 2013

Related U.S. Application Data

(62) Division of application No. 12/562,220, filed on Sep. 18, 2009, now Pat. No. 8,419,696.

(60) Provisional application No. 61/098,164, filed on Sep. 18, 2008.

(51) Int. Cl.
A61M 1/00 (2006.01)

(52) U.S. Cl.
CPC ........... A61M 1/0023 (2013.01); A61M 1/0084 (2013.01); A61M 1/0092 (2014.02);
(Continued)

(58) Field of Classification Search
CPC ......... A61M 1/00; A61M 27/00; A61F 13/02; A61L 15/16
USPC ......... 604/133, 134, 218, 313, 317, 319, 403; 141/26, 67
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 A1 3/1986
AU 745271 4/1999
(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
(Continued)

Primary Examiner — Melanie Hand

(57) ABSTRACT

A reduced pressure treatment system includes a first fluid pathway in communication with a reduced pressure source and a second fluid pathway. The system includes a reduced pressure manifold having a substantially gas impermeable barrier and at least one outer conduit defining a lateral edge of an interior region. The outer conduit and the substantially gas impermeable barrier enclose a portion of the interior region. The outer conduit is in fluid communication with one of the first and second fluid pathways. The outer conduit has at least one opening in fluid communication with the interior region. An inner conduit is at least partially disposed within the interior region and is in fluid communication with another of the first and second fluid pathways. The inner conduit has at least one opening in fluid communication with the interior region.

26 Claims, 8 Drawing Sheets

(52) U.S. Cl.
CPC ............ *A61M1/0031* (2013.01); *A61M 1/0049* (2013.01); *A61M 2205/7509* (2013.01); *A61M 2205/7518* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,961,480 A | 10/1999 | Augustine |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,752,794 B2 | 6/2004 | Lockwood et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0079852 A1 | 4/2006 | Bubb et al. |
| 2007/0233022 A1 | 10/2007 | Henley et al. |
| 2008/0214982 A1* | 9/2008 | Dextradeur et al. .............. 604/8 |
| 2009/0196855 A1 | 8/2009 | Bornemann |
| 2009/0312723 A1 | 12/2009 | Blott et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 2006114648 A2 | 11/2006 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

* cited by examiner

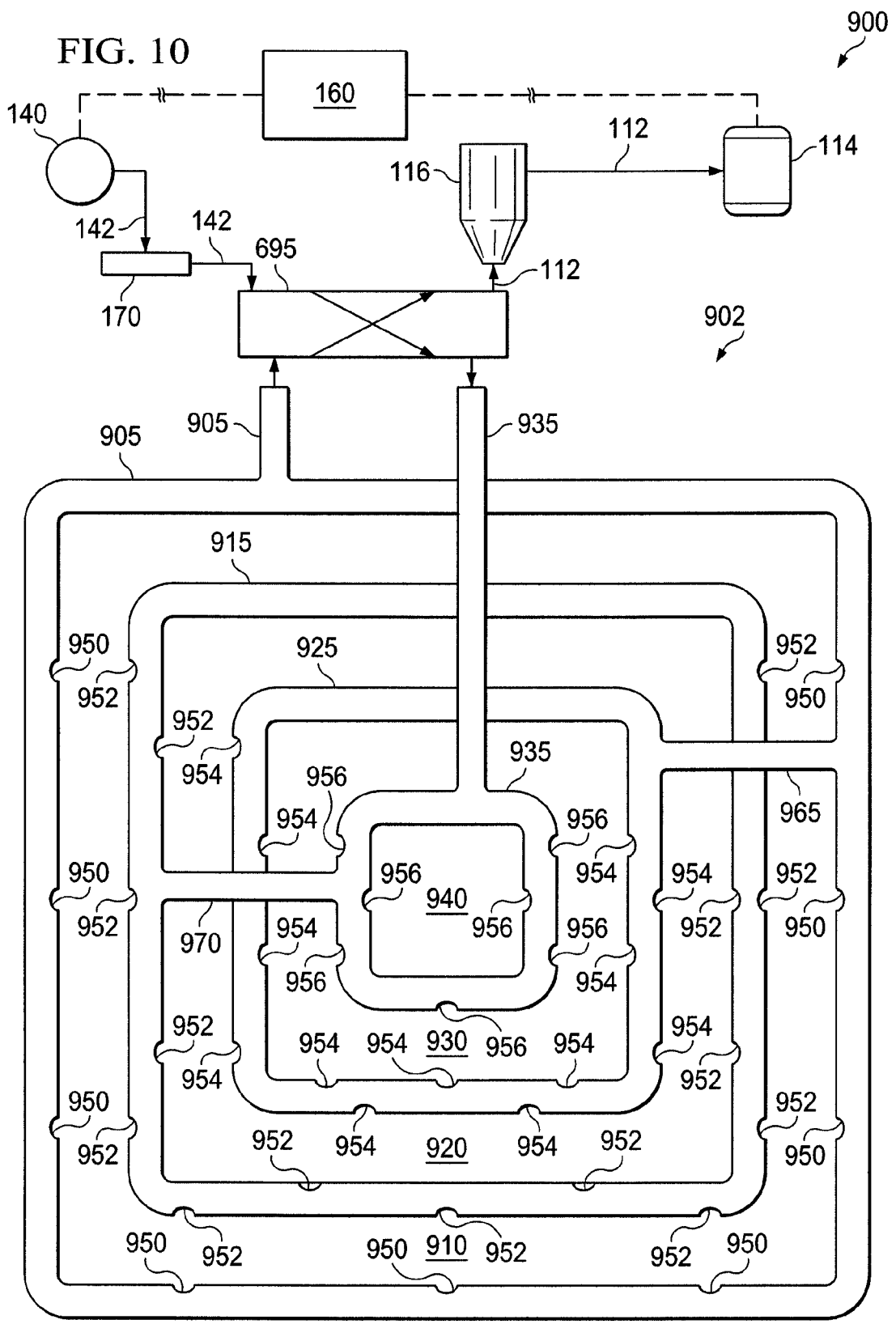

SYSTEM AND METHOD FOR DELIVERING REDUCED PRESSURE TO SUBCUTANEOUS TISSUE

CROSS-REFERENCE TO RELATED APPLICATIONS

This application is a Divisional of U.S. patent application Ser. No. 12/562,220, entitled SYSTEM AND METHOD FOR DELIVERING REDUCED PRESSURE TO SUBCUTANEOUS TISSUE, filed on Sep. 18, 2009, which is a Non-Provisional to and claims the benefit of U.S. Provisional Application No. 61/098,164, filed Sep. 18, 2008, the contents of which are hereby incorporated by reference in their entirety.

BACKGROUND OF THE INVENTION

1. Field of the Invention

The present invention relates generally to tissue treatment systems and in particular to a system for delivering reduced pressure to subcutaneous tissue.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure involves treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied by a reduced pressure source to tissue through a porous pad or other manifold device. In many instances, wound exudate and other liquids from the tissue site are collected within a canister to prevent the liquids from reaching the reduced pressure source.

BRIEF SUMMARY OF THE INVENTION

The problems presented by existing reduced pressure systems and reduced pressure dressings are solved by the systems and methods of the illustrative embodiments described herein. In one illustrative embodiment, a reduced pressure treatment system includes a first fluid pathway and a second fluid pathway, the first fluid pathway being in communication with a reduced pressure source. The system further includes a reduced pressure manifold having a substantially gas impermeable barrier and at least one outer conduit defining a lateral edge of an interior region. The outer conduit and the substantially gas impermeable barrier enclose a portion of the interior region. The outer conduit is in fluid communication with one of the first and second fluid pathways and has at least one opening in fluid communication with the interior region. An inner conduit is at least partially disposed within the interior region and is in fluid communication with another of the first and second fluid pathways. The inner conduit has at least one opening in fluid communication with the interior region.

In another illustrative embodiment, a reduced pressure manifold for applying reduced pressure treatment to a tissue site includes a substantially gas impermeable barrier. An outer conduit is positioned on the first side of the barrier and defines a perimeter around an interior region and is adapted to be fluidly connected to one of a reduced pressure source and a vent source. The outer conduit has at least one opening that is in fluid communication with the interior region. An inner conduit is positioned on a first side of the barrier and extends into the interior region. The inner conduit is adapted to be fluidly connected to another of the reduced pressure source and the vent source and has at least one opening in fluid communication with the interior region.

In another illustrative embodiment, a reduced pressure treatment system includes a reduced pressure source and a vent, source. The system further includes a reduced pressure manifold having a first conduit shaped to define an interior region. The first conduit is in fluid communication with one of the reduced pressure source and the vent source. The first conduit has at least one opening in fluid communication with the interior region. A second conduit is at least partially disposed within the interior region and is in fluid communication with another of the reduced pressure source and the vent source. The second conduit has at least one opening in fluid communication with the interior region.

In yet another illustrative embodiment, a manifold for applying a reduced pressure treatment to a subcutaneous tissue site is provided. The manifold includes a first conduit shaped to define an interior region and being adapted to be fluidly connected to one of a reduced pressure source and a vent source. The first conduit has at least one opening in fluid communication with the interior region. A second conduit is at least partially disposed within the interior region and is adapted to be fluidly connected to another of the reduced pressure source and the vent source. The second conduit has at least one opening that is in fluid communication with the interior region.

In still another illustrative embodiment, a method for delivering reduced pressure to a tissue site is provided. The method includes delivering a fluid to the tissue site through a loop-shaped, first conduit, the first conduit defining a perimeter around an interior region. A reduced pressure is applied to the interior region through a second conduit positioned in the interior region, and tissue healing by products are removed from the interior region through the second conduit.

In another illustrative embodiment, a method for delivering reduced pressure to a tissue site includes applying a reduced pressure to the tissue site through a loop-shaped, first conduit, the first conduit defining a perimeter around an interior region. A fluid is delivered to the interior region through a second conduit positioned in the interior region. Tissue healing by-products are removed from the interior region through the first conduit.

Other features and advantages of the illustrative embodiments will become apparent with reference to the drawings and detailed description that follow.

BRIEF DESCRIPTION OF THE DRAWINGS

FIG. 10 illustrates a schematic top view of a reduced pressure treatment system for providing reduced pressure and fluid to a tissue site according to an illustrative embodiment.

DETAILED DESCRIPTION OF THE PREFERRED EMBODIMENT

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
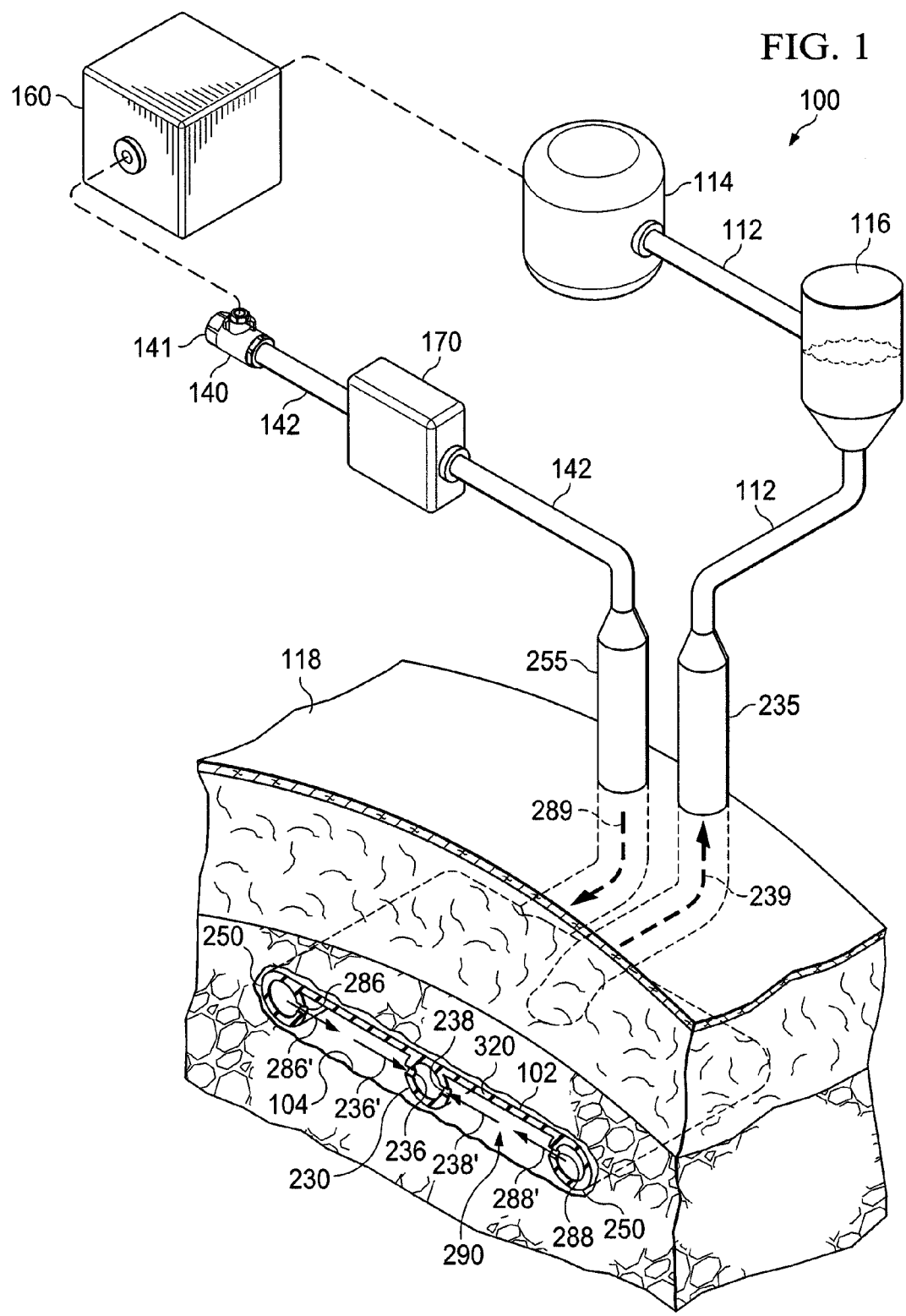
FIG. 1 illustrates a perspective view of a reduced pressure treatment system having a reduced pressure manifold according to an illustrative embodiment.
Figure 2:
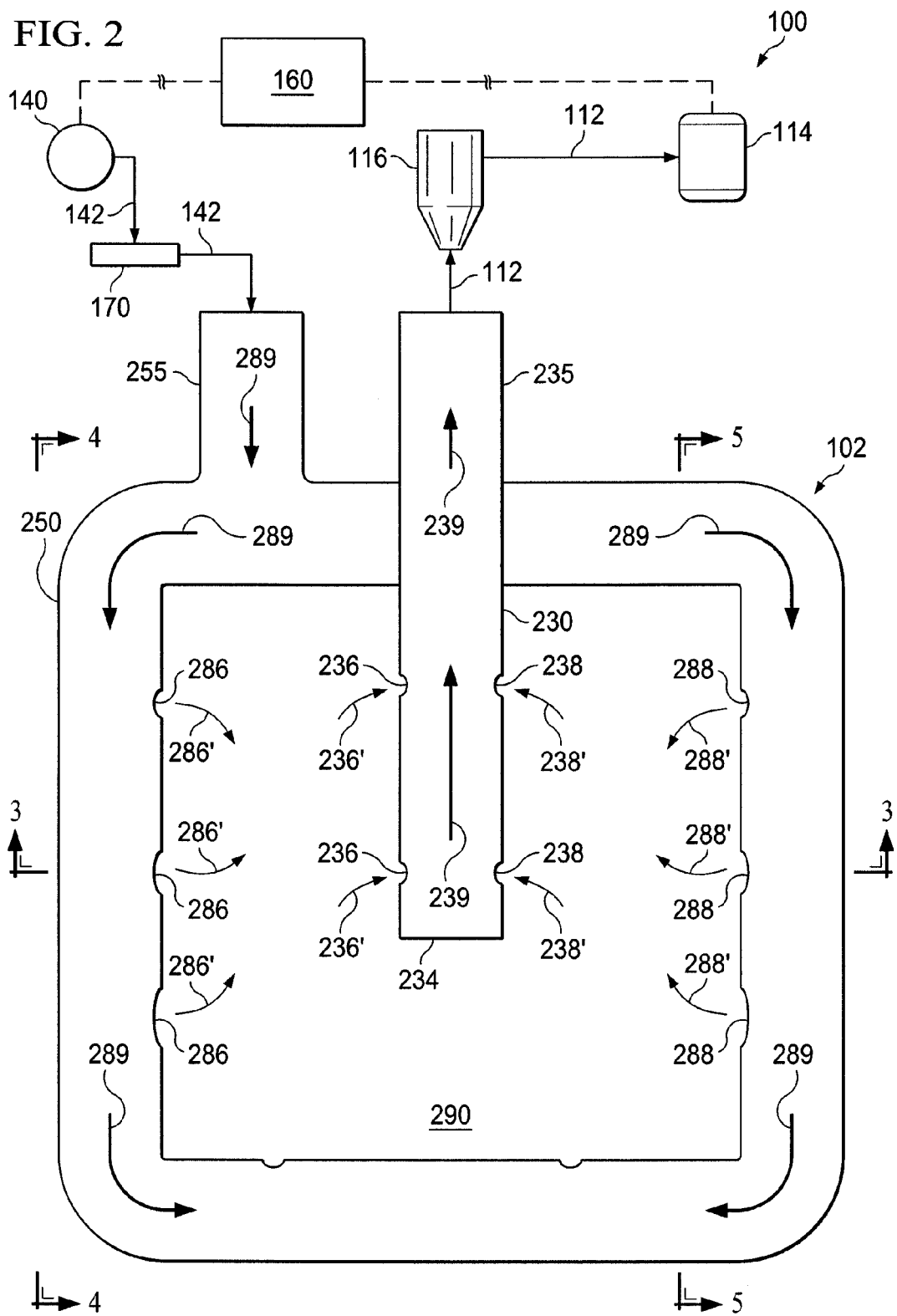
FIG. 2 illustrates a schematic top view of the reduced pressure treatment system of FIG. 1, a barrier of the reduced pressure manifold not shown for purpose of clarity.

Referring now primarily to FIG. 1, an illustrative reduced pressure treatment system 100 includes a reduced pressure manifold 102 to apply a reduced pressure to a tissue site 104. The reduced pressure manifold 102 serves as a manifold for distributing reduced pressure. The term "manifold" as used herein generally refers to a substance or structure that is provided to assist in applying reduced pressure to, delivering fluids to, or removing fluids from a tissue site. The manifold typically includes a plurality of flow channels or pathways to improve distribution of fluids provided to and removed from the tissue site. The reduced pressure manifold 102 that serves as a manifold may include a number of layers as will be described further below.

The tissue site 104 may be the bodily tissue of any human, animal, or other organism, including bone tissue, adipose tissue, muscle tissue, neural tissue, dermal tissue, vascular tissue, connective tissue, cartilage, tendons, ligaments, or any other tissue. While the tissue site 104 may include a wound, diseased tissue, or defective tissue, the tissue site 104 may also be healthy tissue that is not wounded, diseased, or defective. Although the reduced pressure manifold 102 may be used with any tissue site, including open wounds, the reduced pressure manifold 102 is particularly useful when used on subcutaneous tissue sites such as, for example, the subcutaneous cavity and tissue site illustrated in FIG. 1.

The application of reduced pressure to the tissue site 104 may be used to promote the drainage of exudate and other liquids from the tissue site 104, as well as to stimulate the growth of additional tissue. In the case in which the tissue site 104 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. The reduced pressure delivered may be static or varied (patterned or random) and may be delivered continuously or intermittently. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Consistent with the use herein, increases in reduced pressure or vacuum pressure typically refer to a relative reduction in absolute pressure, while decreases in reduced pressure typically refer to an increase in absolute pressure.

Unless otherwise indicated, as used herein, "or" does not require mutual exclusivity.

The reduced pressure is provided to the reduced pressure manifold 102 by a reduced-pressure delivery conduit 112. The reduced-pressure delivery conduit 112 receives reduced pressure from a reduced-pressure source 114. The reduced-pressure source 114 may be any device or subsystem for supplying reduced pressure, including but not limited to a manually operated pump, a powered vacuum pump, a wall vacuum source, or any other device or system capable of supplying a reduced pressure. While the amount and nature of reduced pressure applied to a site will typically vary according to the application, the reduced pressure will typically be between about −5 mm Hg and about −500 mm Hg and more typically between about −100 mm Hg and about −200 mm Hg. In one illustrative embodiment, the reduced pressure source 114 may be a battery-driven vacuum pump. In this example, the pump may use low amounts of power and be capable of operating for an extended period of time on a single charge of the battery.

One or more devices may be fluidly coupled between the reduced pressure manifold 102 and the reduced-pressure source 114. For example, representative device 116 is shown fluidly coupled on a portion of the reduced-pressure delivery conduit 112. The representative device 116 may be a fluid reservoir, or collection member, to hold exudates and other fluids removed. Other illustrative, non-limiting examples of devices 116 that may be included on the reduced-pressure delivery conduit 112 or otherwise fluidly coupled to the reduced-pressure delivery conduit 112 include, without limitation, a pressure sensing or feedback device, a volume detection system, a blood detection system, an infection detection system, a flow monitoring system, or a temperature monitoring system. Some of these devices may be integrally associated with the reduced-pressure source 114 or other aspects of the system 100.

The reduced pressure manifold 102 is adapted to contact or cover the tissue site 104 that is to be treated. As used herein, the term "cover" includes partially or fully covering. Also, a first object that covers a second object may directly or indirectly touch the second object, or may not touch the second object at all.

The reduced pressure manifold 102 is illustrated in FIG. 1 as being positioned at a subcutaneous tissue site. The reduced pressure manifold 102 may be placed at the tissue site either surgically or percutaneously by the use of, for example, laproscopic or endoscopic equipment. When the reduced pressure manifold 102 is placed at a subcutaneous tissue site, the presence of tissue surrounding the cavity in which the reduced pressure manifold 102 is positioned results in a substantially sealed tissue site without the need for a drape or cover as may be required by open-wound, reduced pressure treatment. In the embodiment illustrated in FIG. 1, the reduced pressure delivery conduit 112 passes percutaneously to the reduced pressure manifold 102.

The reduced-pressure delivery conduit 112 may be any tube, conduit, or flow path through which a gas, liquid, gel, or other fluid may flow. The possible embodiments of the reduced-pressure delivery conduit 112 are numerous, and non-limiting examples follow. The reduced-pressure delivery conduit 112 may have any cross-sectional shape, such as a circle, oval, polygon, or any other shape. In addition, the reduced-pressure delivery conduit 112 may be made from any material, and may be either flexible or inflexible. In FIG. 1, the reduced-pressure delivery conduit 112 fluidly couples the reduced pressure manifold 102 to the representative device 116 and the reduced-pressure source 114. However, reduced-pressure delivery conduit 112 may instead directly couple reduced pressure source 114 to the reduced pressure manifold 102. Also; the reduced-pressure delivery conduit 112 may include one or more paths or lumens through which fluid may flow. For example, the reduced-pressure delivery conduit 112 may include two lumens with one lumen being used to deliver reduced pressure and one to monitor pressure to determine the amount of reduced pressure at the tissue site 104.

If the reduced pressure manifold 102 is used with an open wound or tissue site, a sealing member (not illustrated), such as a cover or drape, may be used to seal the reduced pressure manifold 102 at the tissue site The sealing member may be any material that provides a fluid seal over the reduced pressure manifold 102 and a portion of a patient's epidermis 118 or the tissue surrounding the tissue site 104. The sealing member may, for example, be an impermeable or semi-permeable, elastomeric material. "Elastomeric" means having the properties of an elastomer. Generally, an elastomer is a polymeric material that has rubber-like properties. More specifically, most elastomers have elongation rates greater than 100% and a significant amount of resilience. The resilience of a material refers to the material's ability to recover from an elastic deformation. Examples of elastomers, which may be used in a sealing member, include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. In an illustrative embodiment, the sealing member may be a drape such as those drapes used with surgical and other medical procedures.

If a sealing member is used to secure and seal the reduced pressure manifold 102 at an open tissue site, the sealing member may be secured to the surrounding epidermis 118 or tissue using an adhesive, gasket, or other attachment device. A connection member or other tubing adapter may also be used with the sealing member to permit connection with the reduced pressure delivery conduit 112 and to allow communication through the sealing member.

The reduced pressure treatment system 100 further includes a vent source 140 and a fluid delivery conduit 142 fluidly connecting the vent source 140 to reduced pressure manifold 102. A control unit 160 may be operably connected to either or both of the reduced pressure source 114 and the vent source 140 to control delivery of reduced pressure and fluid to the reduced pressure manifold 102. A filter 170 may be fluidly connected between the vent source 140 and the reduced pressure manifold to filter fluid delivered through the fluid delivery conduit 142. More specifically, the filter 170 may prevent ingress of particulates or microbes from the atmosphere from entering the reduced pressure manifold 102 if the vent source 140 is opened to the atmosphere as described below.

In one illustrative embodiment, the vent source 140 is a valve that allows venting of the fluid delivery conduit 142 to atmosphere. Since the tissue site 104 and reduced pressure manifold 102 are typically exposed to a reduced pressure, opening the vent source 140 to atmosphere results in fluid (e.g. air) flowing through a vent port 141 of the vent source 140 and into the fluid delivery conduit 142 toward the reduced pressure manifold 102. The vent source 140 may be any type of valve, but in one illustrative embodiment, the vent source 140 is a valve that is capable of being opened or closed by the control unit 160. In another embodiment, the vent source 140 may be a pump or any other device that is capable of delivering a fluid to the reduced pressure manifold 102. While the vent source 140 may be operated or controlled by electrical means, the vent source 140 instead could be operated by purely mechanical means. For example, the vent source 140 may operate or be controlled based on a differential pressure similar to a relief valve. Alternatively, the vent source 140 may operate or be controlled according to a rate of change in pressure. In one embodiment, the vent source 140 may also be operated or controlled manually by a user.

Similar to the reduced pressure delivery conduit 112, the fluid delivery conduit 142 may be any tube, conduit, or flow path through which a gas, liquid, gel, or other fluid may flow. The fluid delivery conduit 142 may have any cross-sectional shape, such as a circle, oval, polygon, or any other shape. In addition, the fluid delivery conduit 142 may be made from any material, and may be either flexible or inflexible. The fluid delivery conduit 142 may further include one or multiple lumens.

Referring still to FIG. 1, but also to FIGS. 2-5, the reduced pressure manifold 102 is described in more detail. The reduced pressure manifold 102 includes an inner conduit 230 and an outer conduit 250 that may have a loop-shaped configuration. In one embodiment, the outer conduit 250 may be physically arranged or formed to create a closed loop that defines a perimeter of an interior region 290. The interior region 290 is positioned adjacent the tissue site 104 when the reduced pressure manifold 102 is used to administer reduced pressure treatment to the tissue site 104.

A proximal end 235 of the inner conduit 230 may extend outside the interior region 290 to allow fluid connection with the reduced pressure delivery conduit 112 or the fluid delivery conduit 142. A distal end 234 of the inner conduit 230 extends into the interior region 290. The distal end 234 may be open, but in one illustrative embodiment, the distal end 234 is a capped or closed end. The inner conduit 230 includes openings 236, 238 which may be, for example, holes, perforations, or a single slit through the inner conduit 230 within the interior region 290. The outer conduit 250 includes a proximal end 255 to allow fluid connection with the fluid delivery conduit 142 or the reduced pressure delivery conduit 112. The outer conduit 250 includes openings 286, 288, through the outer conduit 250 adjacent the interior region 290.

In the embodiment illustrated in FIGS. 2-5, the inner conduit 230 is fluidly connected to the reduced pressure source 114 and the outer conduit 250 is fluidly connected to the vent source 140. The direction of fluid flow, either gas, liquid, or both, through the conduits 230, 250 is indicated generally by fluid flow arrows. Fluid flow through the inner conduit 230 is indicated by arrows 239, while fluid flow through the outer conduit 250 is indicated by arrows 289. When reduced pressure is applied to the inner conduit 230 and fluid is provided by the vent source 140 to the outer conduit 250, fluid flows through the interior region 290 from the outer conduit 250 to the inner conduit 230. More specifically, fluid flows through the openings 286, 288 of the outer conduit 250 as indicated by fluid flow arrows 286', 288'. Fluid flows through the interior region 290 into the opening 236, 238 of the inner conduit 230 as indicated by fluid flow arrows 236', 238'.

Figure 3:
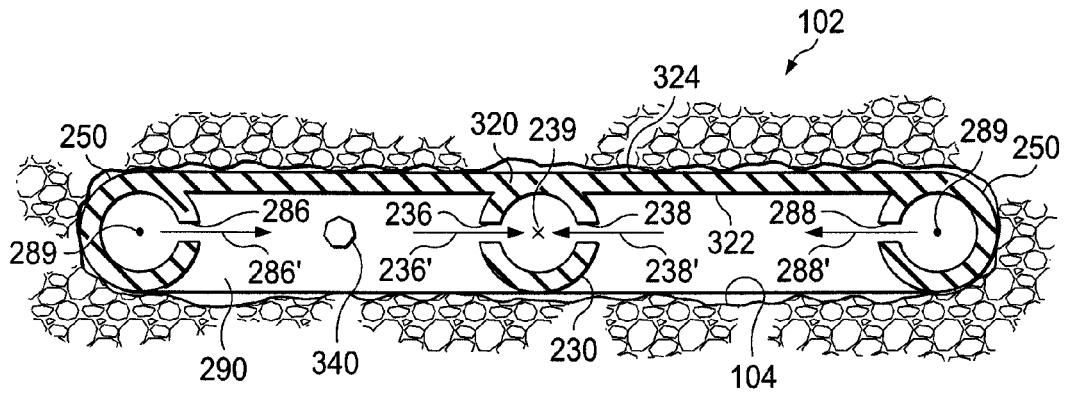
FIG. 3 illustrates a cross-sectional view of the reduced pressure treatment system of FIG. 2 taken along line 3-3 positioned at the tissue site.
Figure 4:
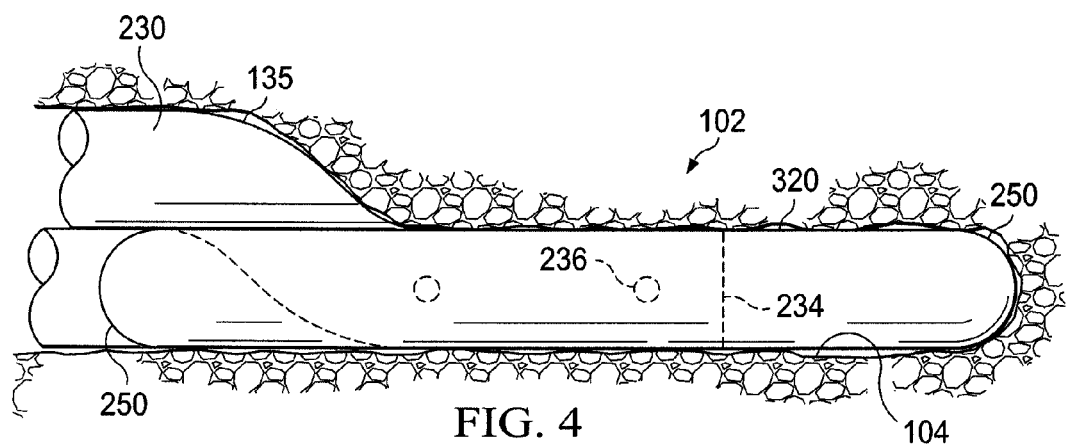
FIG. 4 illustrates a cross-sectional view of the reduced pressure treatment system of FIG. 2 taken along line 4-4 positioned at the tissue site.
Figure 5:
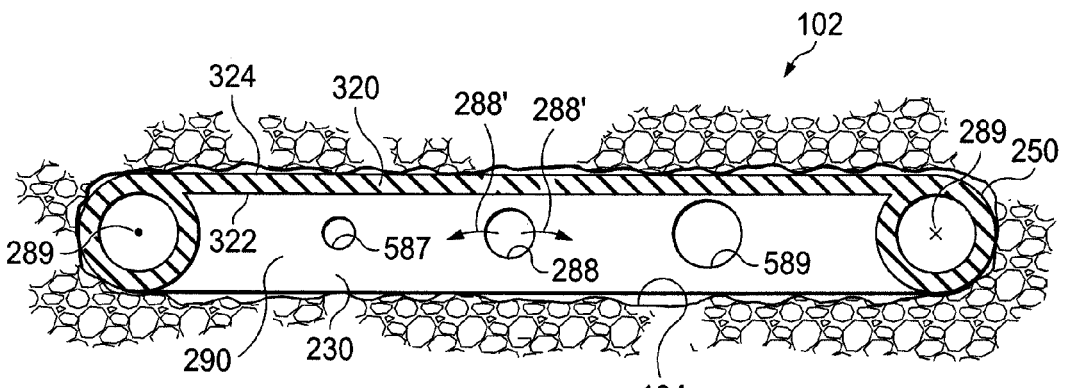
FIG. 5 illustrates a cross-sectional view of the reduced pressure treatment system of FIG. 2 taken along line 5-5 positioned at the tissue site.

Referring more specifically to FIGS. 3-5, the reduced pressure manifold 102 includes a barrier 320 having a first side 322 and a second side 324. The inner conduit 230 and outer conduit 250 are positioned on the first side 322 of the barrier 320. The presence of barrier 320 may separate the interior region 290 from other areas of tissue near the reduced pressure manifold. In one embodiment, the interior region 290 is defined and bordered by the outer conduit 250, the barrier 320, and the tissue site 104. For fluid that flows through the interior region 290 (i.e. fluid that enters through the inner conduit 230 or outer conduit 250, or fluid that is drawn from the tissue site 104), the barrier 320 acts to substantially constrain fluid flow to the area of the interior region 290 and the vicinity around the tissue site 104. The barrier 320 substantially reduces or prevents fluid flow on the second side 324 of the barrier 320. In one embodiment, the barrier may be made of a substantially gas impermeable material. In another embodiment, the barrier 210 may be semi-permeable to gas flow. Examples of materials that could be used for the barrier 320 include without limitation silicone, polyurethane, or any other substantially gas impermeable material.

In operation, the reduced pressure manifold 102 is positioned adjacent or in contact with the tissue site 104. Reduced pressure is supplied to the tissue site 104 and interior region 290 by the reduced pressure source 114. The reduced pressure is delivered through reduced pressure delivery conduit 112 and inner conduit 230 of reduced pressure manifold 102. Due to the relatively confined nature of the subcutaneous tissue site, as well as the presence of the barrier 320, reduced pressure may be maintained at the tissue site 104 such that reduced pressure treatment or therapy is provided. As treatment progresses, granulation tissue growth is stimulated. Wound exudate and other fluids are removed from the tissue site 104 and interior region 290 through the inner conduit 230 and may be collected within a canister such as that represented by representative device 116.

The growth of new tissue and production of exudate and other by-products at the tissue site 104 are capable of hindering treatment if not successfully removed. For example, if wound exudate or blood were to collect within the conduits or at the tissue site 104, the delivery of reduced pressure to the tissue site 104 may be interrupted. The presence of the outer conduit 250 assists in minimizing or preventing the collection of fluids, solids, and other by-products at the tissue site and within the inner conduit 230. By delivering air or other fluids from the vent source 140 to the outer conduit 250 and the interior region 290, fluids, solids, and other by-products may be better dislodged and carried to the inner conduit 230. As illustrated in FIG. 3, the fluid flow represented by arrows 286', 288' assists in carrying wound healing by-products 340 to the inner conduit 230 where the by-products 340 may be removed.

In one embodiment, it may be desired to apply either the reduced pressure, the fluid flow (from the vent source 140), or both intermittently to the reduced pressure manifold 102. Modulation of the flow may be achieved by varying both the upstream and downstream pressures, either manually or automatically through the control unit 160. This modulation, and any induced fluid momentum effects, may further increase the fluidic force applied to the by-products 340.

The barrier 320 of the reduced pressure manifold 102 may further assist in dislodging by-products 340. As previously described, the barrier 320 substantially constrains fluid flow to the area of the interior region 290 and the vicinity around the tissue site 104, which reduces the amount of fluid leaking outside of the interior region 290. This minimization of leakage optimizes flow within the interior region 290 from the outer conduit 250 to the inner conduit 230 as depicted by the fluid flow arrows illustrated in FIG. 3.

Referring more specifically to FIG. 5, in one embodiment, the opening 288 in the outer conduit 250 is one of several holes spaced along the length of the outer conduit 250 for delivering the fluid from the vent source 140. The other openings may be evenly spaced along the length of the outer conduit 250 in order to evenly distribute fluid to the interior region 290 and the tissue site 210. Alternatively, the spacing between the openings may be of varying distances or random. In one illustrative embodiment, the openings may have diameters that generally increase in diameter as further removed from the source of the fluid such as, for example, openings 587 and 589, to more evenly distribute the flow of fluid into the interior region 290.

Figure 6:
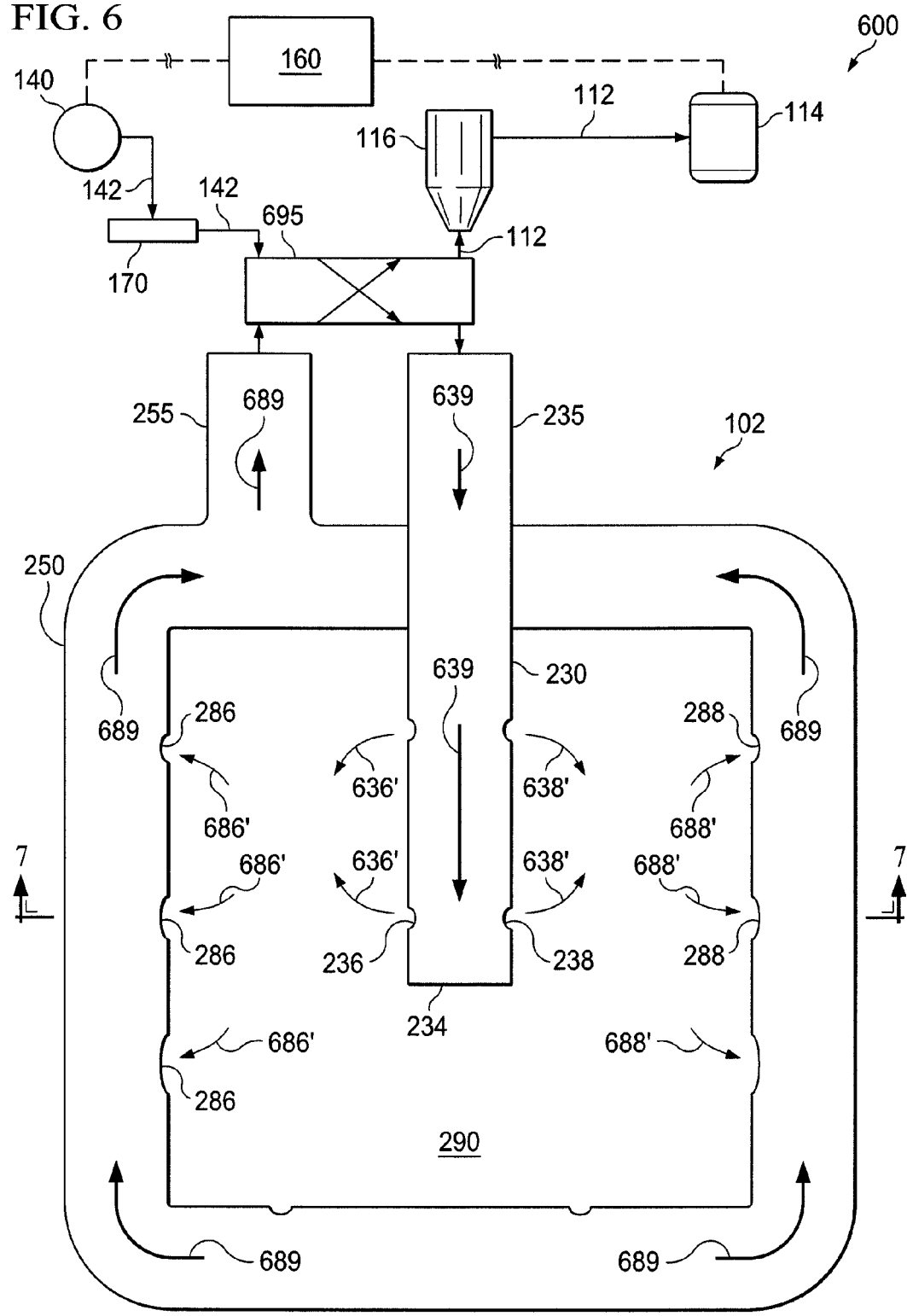
FIG. 6 illustrates a schematic top view of a reduced pressure treatment system for providing reduced pressure and fluid to a tissue site according to an illustrative embodiment, the reduced pressure treatment system having a valve for reversing flow of fluid and reduced pressure.

Referring to FIG. 6, a reduced pressure treatment system 600 sharing some similar elements of reduced pressure treatment system 100 is illustrated. Reduced pressure treatment system 600 includes reduced pressure manifold 102, reduced pressure source 114, representative device 116, reduced pressure delivery conduit 112, vent source 140, filter 170, fluid delivery conduit 142, and control unit 160, all of which may be similar in structure and function to those elements previously described. The reduced pressure treatment system 600 further includes a switching unit or valve 695 fluidly connected between the reduced pressure manifold 102 and both the reduced pressure source 114 and the vent source 140. The switching unit 695 is capable of reversing the flow of fluid within the inner conduit 230 and the outer conduit 250 relative to the flow directions previously described with reference to FIGS. 1-5. As illustrated in FIG. 6, fluid flow within the outer conduit 250 may be such that fluid is removed toward the reduced pressure source 114 as indicated by fluid flow arrows 689. Fluid from the interior region 290 flows into the openings 286, 288 of the outer conduit 250 as indicated by arrows 686', 688', respectively. Fluid flow within the inner conduit 230 may be provided by the vent source 140 and flow toward the interior region 290 as indicated by fluid flow arrows 639. Fluid enters the interior region 290 through the openings 236, 238 of the inner conduit 230 as indicated by arrows 636', 638', respectively.

Figure 7:
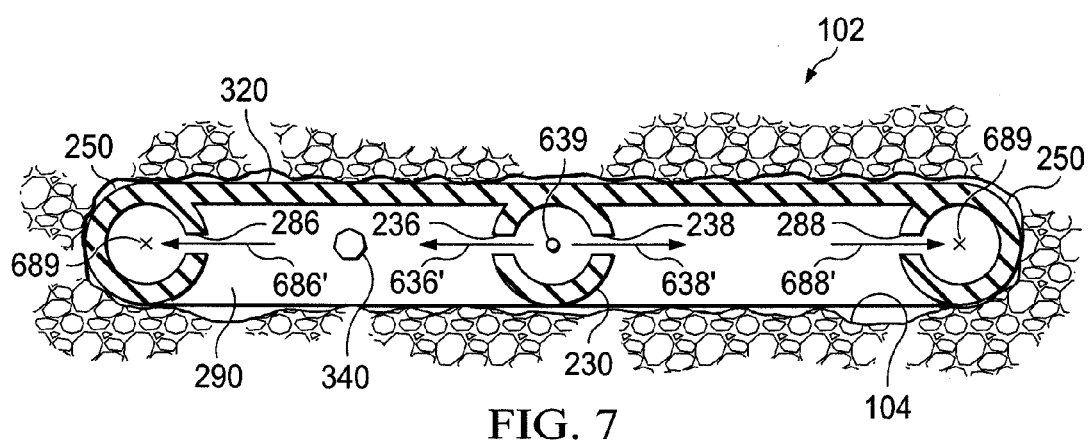
FIG. 7 illustrates a cross-sectional view of the reduced pressure treatment system of FIG. 6 taken along the line 7-7 positioned at the tissue site.

FIG. 7 represents a cross-section view of the reduced pressure treatment system 600 and demonstrates the removal of by-products 340 may occur through the outer conduit 250 as fluid is supplied by the vent source 140 through the inner conduit 230. While the flow of fluids in FIGS. 6 and 7 is illustrated as moving from the inner conduit 230 to the outer conduit 250, the presence of the switching unit 695 permits the fluid flow to be reversed, which in some instances may assist in dislodging or removing by-products 340. In one embodiments, it may be desirable to regularly or intermittently reverse the flow of fluids through the reduced pressure manifold 102.

Figure 8:
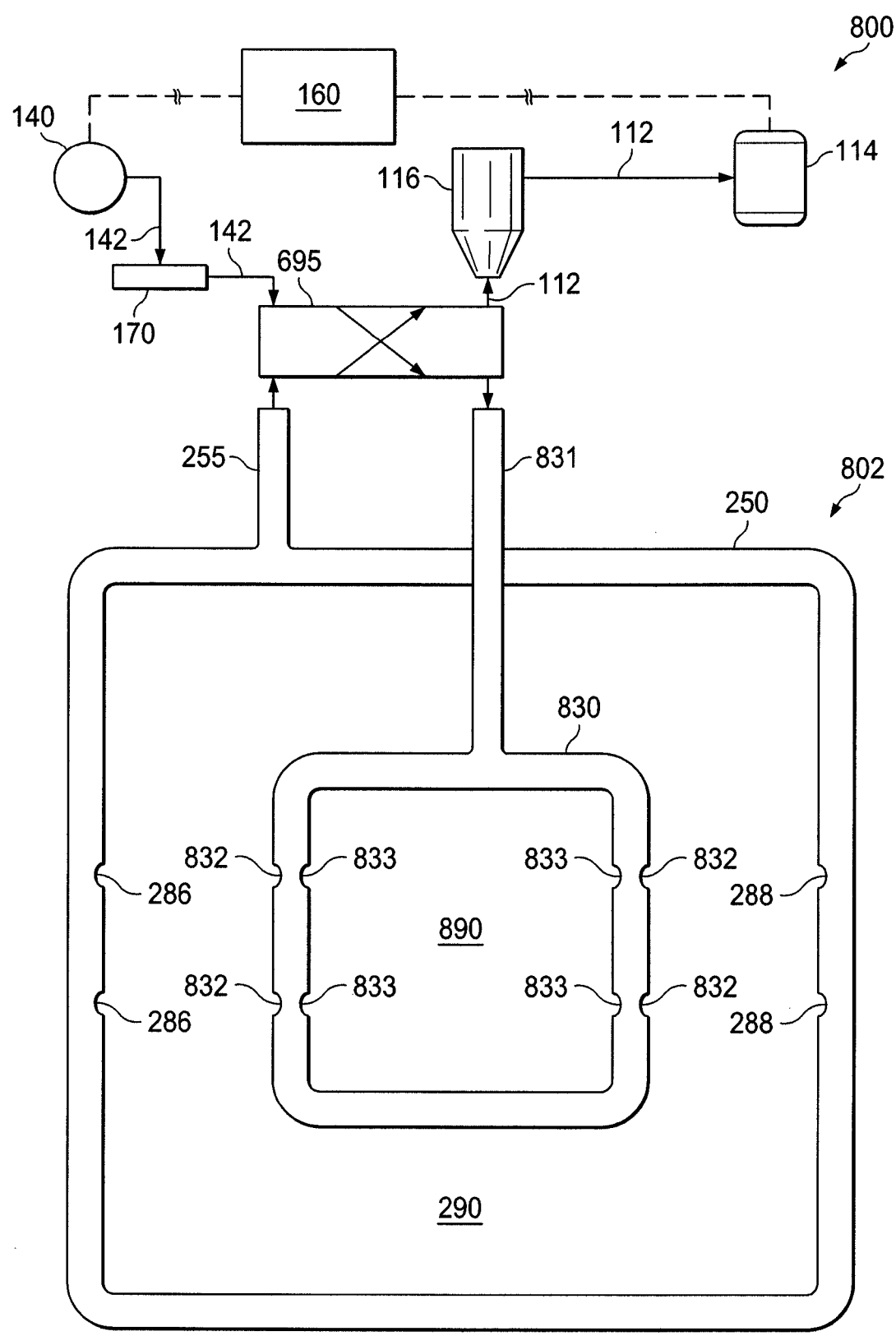
FIG. 8 illustrates a schematic top view of a reduced pressure treatment system for providing reduced pressure and fluid to a tissue site according to an illustrative embodiment.

Referring to FIG. 8, a reduced pressure treatment system 800 includes some similar elements to that of reduced pressure treatment system 100. Reduced pressure treatment system 800 includes a reduced pressure manifold 802, which is a modified version of the reduced pressure manifold 102. The reduced pressure manifold 802 includes an inner conduit 830 having a distal end in a closed-loop configuration. The distal end of the inner conduit 830 extends into the interior region 290, and the looped configuration of the inner conduit 830 defines a second interior region 890. The inner conduit 830 includes a proximal end 831 that may be fluidly connected to either reduced pressure source 114 or vent source 140 through switching unit 695. As described above, the fluid flow through the inner conduit 830 and the outer conduit 180 may be switched to cause fluid to flow in either direction within the interior region 290. The inner conduit 830 includes openings 832, 833 which may be, for example, holes, perforations, or a single slit through the inner conduit 830 adjacent either or both of the interior region 290 and the second interior region 890. The openings 832 in the closed-loop conduit generally face the openings 286, 288 in the outer conduit 250, thereby creating a flow of fluids through the interior region 290 as described previously with reference to FIGS. 1-5. The openings 833 of the inner conduit 830 function in a similar manner with the openings 286, 288 of the outer conduit 250, but create a flow of fluids over a longer path extending more deeply into the center of the second interior region 890.

Figure 9:
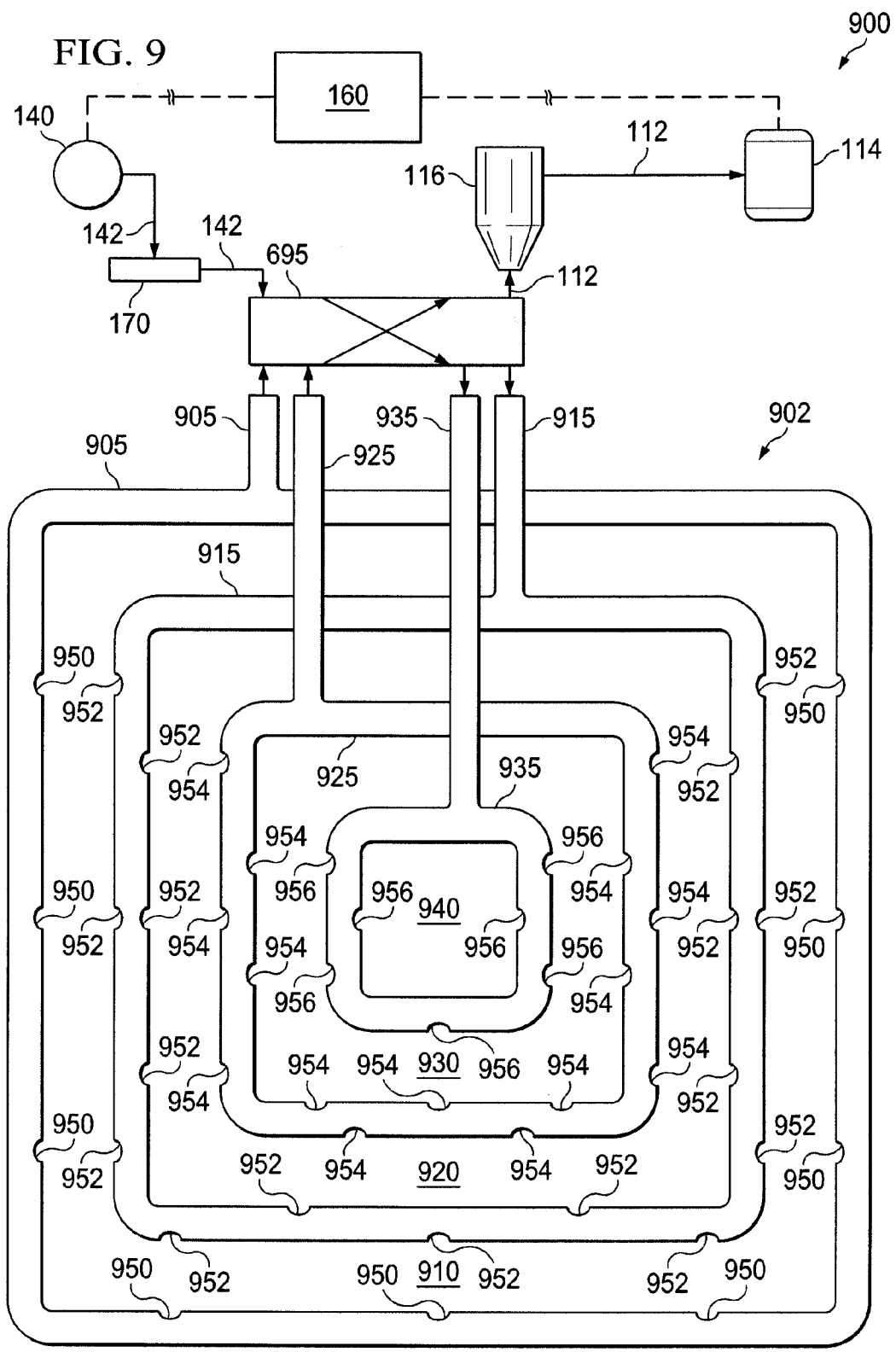
FIG. 9 illustrates a schematic top view of a reduced pressure treatment system for providing reduced pressure and fluid to a tissue site according to an illustrative embodiment.

Referring to FIG. 9, a reduced pressure treatment system 900 includes some similar elements to that of reduced pressure treatment system 100. Reduced pressure treatment system 900 includes a reduced pressure manifold 902, which is a modified version of the reduced pressure manifold 102. Instead of only including a single inner conduit and a single outer conduit, the reduced pressure manifold 902 illustrated in FIG. 9 includes a first conduit 905 defining a first interior region 910, a second conduit 915 positioned within the first interior region 910 and defining a second interior region 920, a third conduit 925 positioned within the second interior region 920 and defining a third interior region 930, and a fourth conduit 935 positioned within the third interior region 930 and defining a fourth interior region 940. Each of the first, second, third, and fourth conduits 905, 915, 925, 935 includes a closed-loop configuration. Each of the first, second, third, and fourth conduits 905, 915, 925, 935 also includes holes, apertures, or openings 950, 952, 954, 956, respectively, as previously described to allow fluid communication with holes in adjacent conduits and with the interior regions 910, 920, 930, 940.

In the embodiment illustrated in FIG. 9, the first conduit 905 and the third conduit 925 are both individually connected to one of the reduced pressure source 114 and the vent source 140. The second conduit 915 and the fourth conduit 935 are both individually connected to another of the reduced pressure source 114 and the vent source 140. The particular configuration involving which conduit is connected to which of the reduced pressure source and the vent source could vary. A switching unit similar to switching unit 695 may also be used to reverse fluid flow within one or more of the conduits.

The reduced pressure manifold 902 is configured as a plurality of nested tubes to provide increased fluid communication within the interior regions 910, 920, 930, 940. The reduced pressure manifold 902 doubles the number of conduits used in reduced pressure manifold 802, and additional conduits could be added as desired. By increasing the number of conduits used with the reduced pressure manifold 902, the, manifold 902 is capable of covering a larger tissue site or providing greater fluid control in a smaller tissue site.

Referring to FIG. 10, the reduced pressure manifold 902 of FIG. 9 is illustrated with one principal modification. Instead of the conduits 905, 915, 925, 935 each being individually connected to the reduced pressure source 114 or the vent source 140, in the embodiment illustrated in FIG. 10, certain conduits are connected by bridging conduits. For example, the first conduit 905 is connected by a bridging conduit 965 to the third conduit 925. This allows reduced pressure or fluids delivered to the first conduit 905 to also be delivered to the third conduit 925. The second conduit 915 is connected by a bridging conduit 970 to the fourth conduit 935. This allows reduced pressure or fluids delivered to the second conduit 915 to also be delivered to the fourth conduit 935.

As shown, the embodiments described above contemplate a reduced pressure manifold for delivering reduced pressure to tissue, particularly subcutaneous tissue. Moreover, these embodiments contemplate such a reduced pressure manifold that uses a connecting conduit that may be used to create a pressure gradient that moves fluid into a inner conduit and facilitates removal of tissue healing by-products, such as blood and coagulum. Such a reduced pressure manifold, when integrally attached to a barrier sheet further isolates reduced pressure on one side of the barrier sheet. Application of controlled, varying pressure in the inner conduit and the connecting conduit induces stronger pressure gradients and fluid forces that further facilitate removal of tissue healing by-products. An optional filter in the connecting conduit pathway may be useful to prevent microbes from infiltrating a tissue site.

Alternative or additional embodiments may include interleaved vent and pressure conduits, or surface features on a barrier sheet that further direct flow toward a inner conduit. Multiple, independent connecting conduits may be activated and controlled separately to redistribute fluid flow along a barrier sheet. Medicinal fluids may also be introduced into the connecting conduit to facilitate tissue growth or treatment.

It should be apparent from the foregoing that an invention having significant advantages has been provided. While the invention is shown in only a few of its forms, it is not just limited but is susceptible to various changes and modifications without departing from the spirit thereof.

I claim:

1. A method for delivering reduced pressure to a tissue site, the method comprising:
   delivering a fluid to the tissue site through a loop-shaped, first conduit, the first conduit defining a perimeter around an interior region;
   applying a reduced pressure to the interior region through a second conduit positioned in the interior region;
   removing tissue healing by products from the interior region through the second conduit; and
   constraining fluid flow to the interior region with a barrier coupled to the first conduit.

2. The method of claim 1, wherein the tissue site is a subcutaneous tissue site.

3. The method of claim 1, wherein the second conduit is looped shaped and defines a second interior region.

4. The method of claim 3 further comprising:
delivering the fluid to the tissue site through a loop-shaped, third conduit positioned within the second interior region, the third conduit defining a perimeter around a third interior region;
applying the reduced pressure to the third interior region through a fourth conduit positioned in the third interior region; and
removing tissue healing by products from the third interior region through the fourth conduit.

5. The method of claim 1 further comprising:
varying the amount of the fluid delivered through the first conduit.

6. The method of claim 4 further comprising:
varying the amount of the fluid delivered through the first conduit and the third conduit.

7. The method of claim 1 further comprising:
intermittently ceasing delivery of the fluid through the first conduit.

8. The method of claim 4 further comprising:
intermittently ceasing delivery of the fluid through the first conduit and the third conduit.

9. The method of claim 1, further comprising filtering the fluid delivered through the first conduit.

10. The method of claim 1, further comprising switching the delivery of the fluid and the application of the reduced pressure such that the fluid is delivered through the second conduit and the reduced pressure is applied through the first conduit.

11. The method of claim 1, wherein the loop shaped, first conduit has at least one cylindrical portion adjacent the interior region.

12. A method for delivering reduced pressure to a tissue site, the method comprising:
applying a reduced pressure to the tissue site through a loop-shaped, first conduit, the first conduit defining a perimeter around an interior region;
delivering a fluid to the interior region through a second conduit positioned in the interior region;
removing tissue healing by-products from the interior region through the first conduit; and
constraining fluid flow to the interior region with a barrier coupled to the first conduit.

13. The method of claim 12, wherein the tissue site is a subcutaneous tissue site.

14. The method of claim 12, wherein the second conduit is looped shaped and defines a second interior region.

15. The method of claim 14 further comprising:
applying the reduced pressure to the tissue site through a loop-shaped, third conduit positioned within the second interior region, the third conduit defining a perimeter around a third interior region;
delivering the fluid to the third interior region through a fourth conduit positioned in the third interior region; and
removing tissue healing by products from the third interior region through the third conduit.

16. The method of claim 12 further comprising:
varying the amount of the fluid delivered through the second conduit.

17. The method of claim 15 further comprising:
varying the amount of the fluid delivered through the second conduit and the fourth conduit.

18. The method of claim 12 further comprising:
intermittently ceasing delivery of the fluid through the second conduit.

19. The method of claim 15 further comprising:
intermittently ceasing delivery of the fluid through the second conduit and the fourth conduit.

20. The method of claim 12, further comprising filtering the fluid delivered through the second conduit.

21. The method of claim 12, further comprising switching the delivery of the fluid and the application of the reduced pressure such that the fluid is delivered through the first conduit and the reduced pressure is applied through the second conduit.

22. The method of claim 12, wherein the loop shaped, first conduit has at least one cylindrical portion adjacent the interior portion.

23. The method of claim 1, wherein the first conduit has a closed loop-shape.

24. The method of claim 12, wherein the first conduit has a closed loop-shape.

25. A method for delivering reduced pressure to a tissue site, the method comprising:
delivering a fluid to the tissue site through a loop-shaped, first conduit, the first conduit defining a perimeter around a first interior region;
applying a reduced pressure to the first interior region through a loop-shaped, second conduit positioned in the first interior region, the second conduit defining a second interior region;
removing tissue healing by products from the first interior region through the second conduit;
delivering the fluid to the tissue site through a loop-shaped, third conduit positioned within the second interior region, the third conduit defining a perimeter around a third interior region;
applying the reduced pressure to the third interior region through a fourth conduit positioned in the third interior region; and
removing tissue healing by products from the third interior region through the fourth conduit.

26. A method for delivering reduced pressure to a tissue site, the method comprising:
applying a reduced pressure to the tissue site through a loop-shaped, first conduit, the first conduit defining a perimeter around a first interior region;
delivering a fluid to the interior region through a loop-shaped second conduit positioned in the first interior region, the second conduit defining a second interior region;
removing tissue healing by-products from the interior region through the first conduit;
applying the reduced pressure to the tissue site through a loop-shaped, third conduit positioned within the second interior region, the third conduit defining a perimeter around a third interior region;
delivering the fluid to the third interior region through a fourth conduit positioned in the third interior region; and
removing tissue healing by products from the third interior region through the third conduit.

* * * * *